(12) United States Patent
Marsche et al.

(10) Patent No.: US 7,577,064 B2
(45) Date of Patent: Aug. 18, 2009

(54) MICROPLATE READER WITH INTELLIGENT FILTER SLIDE

(75) Inventors: Robert Marsche, Bad Vigaun (AT); Wolfgang Fuchs, Salzburg (AT); Harald Gebetsroither, Grödig (AT)

(73) Assignee: Tecan Trading AG, Mannedorf (CH)

( * ) Notice: Subject to any disclaimer, the term of this patent is extended or adjusted under 35 U.S.C. 154(b) by 572 days.

(21) Appl. No.: 11/456,610

(22) Filed: Jul. 11, 2006

(65) Prior Publication Data

US 2007/0035732 A1 Feb. 15, 2007

(30) Foreign Application Priority Data

Jul. 11, 2005 (CH) .................................... 1148/05

(51) Int. Cl.
*G11B 7/00* (2006.01)
*G01J 1/10* (2006.01)
(52) U.S. Cl. ..................... 369/47.1; 356/417
(58) Field of Classification Search ........................ None
See application file for complete search history.

(56) References Cited

U.S. PATENT DOCUMENTS

| 5,557,544 | A | 9/1996 | Simon et al. | |
| 5,892,458 | A | 4/1999 | Anderer et al. | |
| 6,313,471 | B1 | 11/2001 | Giebeler et al. | |
| 7,170,597 | B1 * | 1/2007 | Hooper et al. | 356/317 |
| 2005/0232821 | A1 * | 10/2005 | Carrillo et al. | 422/100 |

FOREIGN PATENT DOCUMENTS

| EP | 0 933 624 | 2/1998 |
| EP | 1 291 626 | 9/2002 |
| EP | 1 387 162 | 7/2003 |
| EP | 1387162 | 2/2004 |
| WO | WO98/54077 | 12/1998 |

\* cited by examiner

*Primary Examiner*—Muhammad N. Edun
(74) *Attorney, Agent, or Firm*—Notaro & Michalos P.C.

(57) ABSTRACT

Microplate reader (21) with a computer for controlling the components of said microplate reader (21), comprising a light source (15) for emitting light for irradiating samples (22) or transmitting light through samples (22), and a filter slide (1) situated in the excitation or detection beam path. The microplate reader (21) in accordance with the invention is characterized in that said filter slide (1) comprises an electronic memory (4) for recording and/or retrieving filter-specific data, with said filter-specific data comprising the number and intensity of the light flashes impinging upon a certain filter (2) of said filter slide (1) and/or the intensity and duration of all exposures performed, and that said filter slide (1) comprises a contact point (5,7) jointly with the microplate reader (21) for transmitting such filter-specific data from the computer to the electronic memory (4) of the filter slide (1) and for retrieving such filter-specific data with the computer. According to the method in accordance with the invention for acquiring filter-specific data in a filter slide (1) of such a microplate reader (21), filter-specific data which comprise the number and intensity of the light flashes impinging upon a specific filter (2) of said filter slide (1) and/or the intensity and duration of all exposures performed are transmitted by the computer via a contact point common to said filter slide (1) and the microplate reader (21) to an electronic memory (4) of said filter slide (1) and/or are retrieved with the computer from said electronic memory (4).

14 Claims, 2 Drawing Sheets

MICROPLATE READER WITH INTELLIGENT FILTER SLIDE

The invention relates to a microplate reader with a computer for controlling the components of said microplate reader, comprising a light source for emitting light for irradiating or transmitting light through samples, and a filter slide situated in the excitation or detection beam path.

Devices for irradiating samples or transmitting light through samples which can be characterized by light penetrating the samples (transmission), the light reflected by the samples (reflection), light initiated on or in the sample (fluorescence) or light emitted by the samples themselves (luminescence) have long been known as microscopes, spectrophotometers, fluorometers and the like. The light that penetrates the sample during the irradiation or is reflected by the same or the fluorescence initiated on or in the sample will be designated below as "light originating from the sample" and will be measured for example by one or several photodetectors. The use of different optical filters for influencing light rays with which the samples are radiated or light that is transmitted through the same (so-called immission filters) is known. Similarly, emission filters are known which influence the light emitted by the samples. Especially user-friendly are filter slides which comprise at least one such filter, but preferably several such optical filters, which can be moved with a defined movement into the beam path. Two principal variants of filter slides are known from the prior art: EP 1 387 162 A1 discloses a linearly displaceable filter carriage with six filters or mirrors. Rotatable filters with up to sixteen filters are known from U.S. Pat. No. 6,313,471.

In biochemical screening methods of biotechnological or pharmaceutical research, biochemical reactions are preferably performed in small vessels, so that only small volumes of the educts required for performing the tests need to be used. Microplates with a plurality of 24, 96, 384 or 1536 wells have proven their worth, in which such tests can be performed in the smallest space and in a large number. Measuring methods for detecting the results of biochemical reactions in the wells of such microplates are currently performed in so-called microplate readers. Such microplate readers are preferably equipped with a light source in the form of a flash lamp with which strong light pulses can be issued to a sample where they initiate photoluminescence (phosphorescence or fluorescence) of the sample. Most recent microplate readers such as devices distributed under the name GENios™ Pro oder Infinite™ 200 by the applicant can measure fluorescence, luminescence and also absorbence of a sample. Further or alternative microplate readers comprise a CW lamp (CW=continuous wave) such as a halogen, xenon, mercury or deuterium lamp, or a laser or laser diodes, with which longer exposure times with intensive light are possible.

Due to the numerous possible applications, a large number of filters such as color filters, neutral density filters, polarization filters, dichroic filters are used which differ with respect to a certain wavelength or a certain wavelength range, a certain intensity, a certain polarization direction in which the light waves can penetrate the filter. Especially filters used for irradiating samples with high light intensities such as light flashes and the like will bleach out with continued use, so that they no longer allow the light quality to reach the sample which corresponds to their original definition. Experience has shown that each filter needs to be replaced after a certain radiation load or after a certain time of use.

From U.S. Pat. No. 5,557,544 an analytical spectrometer is known, comprising a permanently installed central computer and exchangeable components such as radiation source, detector, beam splitter, filter and external probe. All these components comprise a readable data medium with encoded data characterizing the respective components, which data relate to the history and/or current properties of the respective components such as operating time, parameters influencing the ageing of components or its calibration curves. These data are continually updated via the central computer, so that directly after the installation of such a component in another spectrometer the current data with the operational state are displayed.

The present invention is therefore based on the object of providing an alternative microplate reader with a filter slide which facilitates the replacement and checking of the individual filters.

This object is achieved in such a way that a microplate reader is proposed which comprises a computer for controlling the components of said microplate reader, a light source for emitting light for irradiating samples or transmitting light through samples, and a filter slide situated in the excitation or detection beam path. The microplate reader in accordance with the invention is characterized in that said filter slide comprises an electronic memory for recording and/or retrieving filter-specific data, with said filter-specific data comprising the number and intensity of the light flashes impinging upon a certain filter of said filter slide and/or the intensity and duration of all exposures performed. The microplate reader in accordance with the invention is further characterized in that said filter slide comprises a contact point together with the microplate reader for transmitting such filter-specific data from the computer to the electronic memory of the filter slide or for retrieving such filter-specific data with the computer.

Additional, preferred and inventive features of said microplate reader with intelligent filter slide in accordance with the invention are obtained from the respective dependent claims.

Advantages arising from the use of the microplate reader with intelligent filter slide in accordance with the invention comprise the following aspects:

The number of light flashes which are sent through a special filter can be counted, stored individually in the electronic memory of the filter slide for each individual filter and can be retrieved again.

The stored data of use are specifically assigned to a filter, so that there is no confusion and the specific period of use can be used up to the maximum point without being exceeded. The issuing of state and alarm notifications depending on the state of use of the individual filters can be provided.

The filter-specific data preferably also comprise the precise and individual filter specifications, so that there cannot be any confusion as to the filters used for a specific application.

The filter slides can be checked by the laboratory staff as well as by the supplier and especially by the service staff as to their remaining service life. Warranty and service jobs can be defined clearly by a unique identification of each individual filter.

The stored data are now inseparably linked to the filter slide or the filters mounted on the same, so that the same filter carriage can be used in several devices and, as required, even in different ones without having to change the settings in the devices.

The microplate reader with filter slide in accordance with the invention is now explained in closer detail by reference to schematic drawings of exemplary embodiments which do not limit the scope of the invention, wherein.

Figure 1:
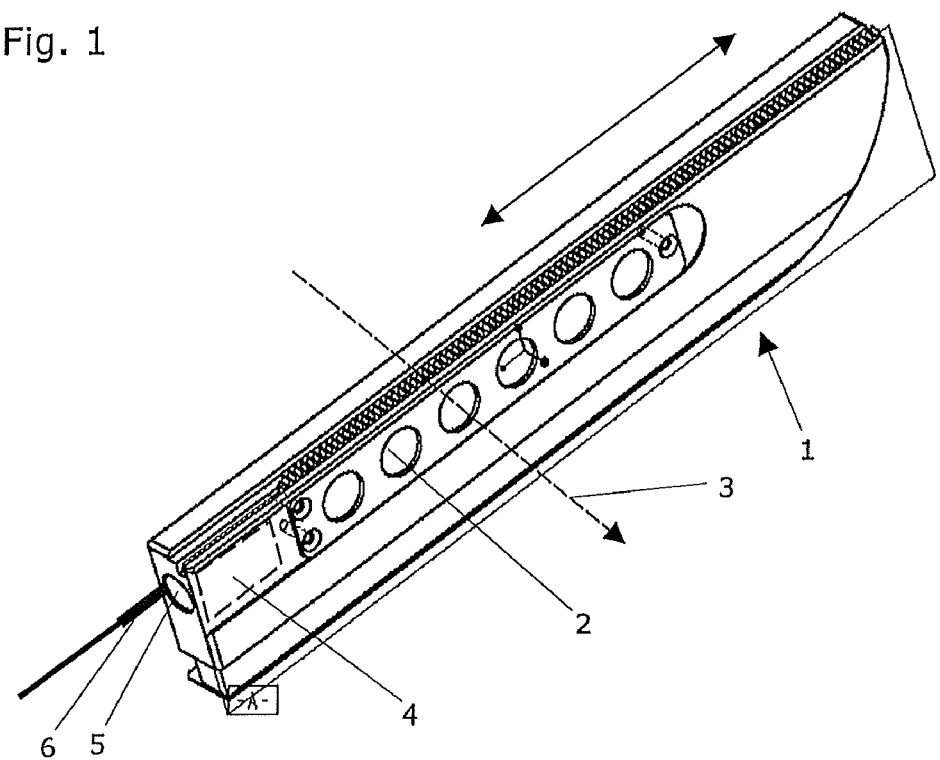
FIG. 1 shows a three-dimensional representation of a filter slide according to a first embodiment.

FIG. 1 shows a three-dimensional representation of a filter slide of the microplate reader in accordance with the invention, according to a first embodiment. The filter slide 1 comprises at least one optical filter 2. In actual fact, the illustrated filter slide 1 comprises six optical filters 2 for influencing light rays 3. Said light rays 3 can be used for irradiating samples or for transmission through samples or for influencing light which is reflected by the samples. The filter slide 1 in accordance with the invention comprises an electronic memory 4 for recording or retrieving filter-specific data and a contact point 5 for transmitting or retrieving such data. The contact point 5 is contacted in this case by a single wire 6 and is thus a so-called "single-wire contact". Said single-wire contact is preferably arranged as a spring contact, but it can also be arranged as a plug-in contact (not shown). The double arrow indicates the direction in which the filter slide 1 can be displaced in order to bring the one or other filter 2 into the light ray 3. The electronic memory 4 is preferably an EEPROM which is fixed in the filter slide and which is electrically connected with the contact point 5. Instead of an EEPROM (Electrically Erasable Programmable Read Only Memory) it is also possible to use other electronic memories such as FEPROM (Flash Erasable Programmable Read Only Memory), UVEPROM (Ultraviolet Erasable Programmable Read Only Memory) and the like. The important aspect in all these cases is that the electronic memory cannot be intentionally influenced or overwritten by the end user, i.e. the user of the apparatus in accordance with the invention.

Figure 2:
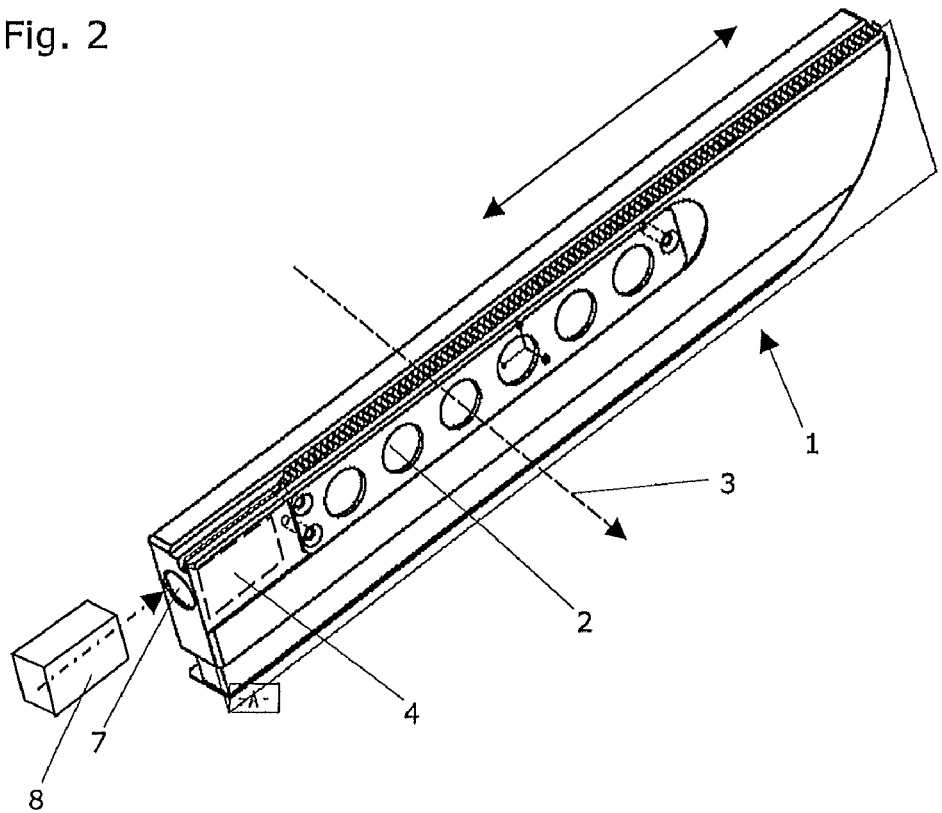
FIG. 2 shows a three-dimensional representation of a filter slide according to a second embodiment.

FIG. 2 shows a three-dimensional illustration of a filter slide of the microplate reader in accordance with the invention, according to a second embodiment. The filter slide 1 comprises at least one optical filter 2. In actual fact, the illustrated filter slide 1 comprises six optical filters 2 for influencing light rays 3. Said light rays 3 can be used for irradiating samples or for transmission through samples or for influencing light which is reflected by the samples. The filter slide 1 in accordance with the invention comprises an electronic memory 4 for recording or retrieving filter-specific data and a contact point 7 for transmitting or retrieving such data. Contact with the contact point 7 is established by a transmitter 8 by means of electromagnetic radiation, preferably in the form of light or via a radio frequency. The double arrow indicates the direction in which the filter slide 1 can be displaced in order to bring the one or other filter 2 into the light ray 3. The electronic memory 4 is preferably in this case an RFID tag which is fixed in the filter slide and which is electrically connected with the contact point 7. Contact point 7 is arranged here as a transmitter/receiver for radio frequency or light information. As an alternative to such radio frequency identification labels (RFID=Radio Frequency Identification) it is also possible to use other systems with an electronic memory or a transmitter for wireless transmission of stored information, as are used for example in security technology (door-locking systems) or transport technology (e.g. in ski lifts and chair lifts) in the form of access cards or wrist watches (such as Swatch® for example) with integrated antennas.

The electronic memory 4 can also comprise, instead of the illustrated EEPROMs with fixed contact, an RFID transponder or a RuBee transceiver which are both suitable for contactless transmission of data. The generally known RFID transponders which operate with radio frequency (RF, e.g. 900 MHz) or ultrahigh frequency (UHF) send and receive radio signals, whereas the latest RuBee transceivers work at wavelengths below 450 KHz, and send and receive signals which are mainly based on magnetism. Passive RFID transponders can receive approximately 100 (RF) or 150-200 (UHF) messages per second, the active RuBee transceivers however only approximately 10 messages per second. A visual link to the contact point 7 which is common to the microplate reader and the filter slide 1 is unnecessary in any case.

Figure 3:
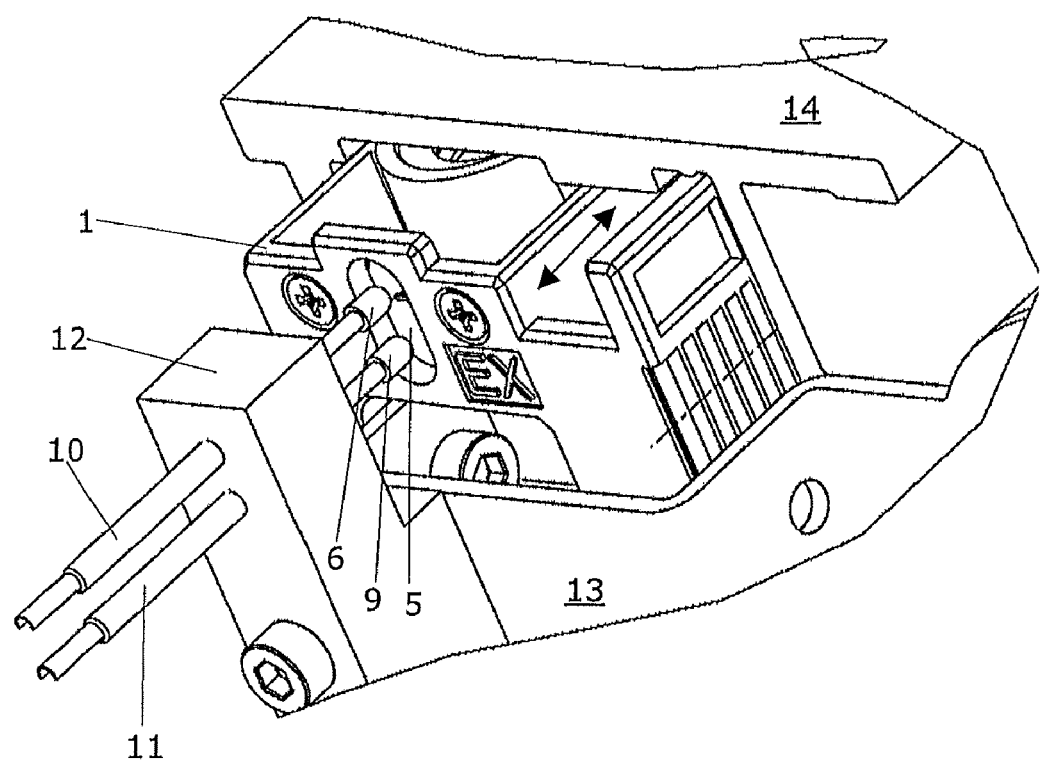
FIG. 3 shows a three-dimensional representation of a filter slide according to a third embodiment.

FIG. 3 shows a three-dimensional representation of a filter slide of the microplate reader in accordance with the invention, according to a third embodiment. The filter slide 1 comprises at least one optical filter 2 for influencing light rays 3. Said light rays 3 can be used for irradiating samples or for transmission through samples or for influencing light which is reflected by the samples. The filter slide 1 in accordance with the invention comprises an electronic memory 4 (not shown) for recording or retrieving filter-specific data and a contact point 5 for transmitting or retrieving such data. Contact is established with the contact point by two wires 6,9 and it is thus a so-called "two-wire contact". Said two-wire contact is preferably arranged as a spring contact. It can also be arranged as a plug-in contact (not shown). The double arrow indicates the direction in which the filter slide 1 can be displaced in order to bring the one or other filter 2 into the light ray 3. The electronic memory 4 is preferably an EEPROM which is fixed in the filter slide and which is electrically connected with the contact point 5.

The wires 6,9 in FIG. 3, but also the wire 6 in FIG. 1 or the transmitter 8 are supplied with data via a feed line 10,11 connected to a computer (not shown). Said feed lines 10,11 and the associated contact wires 6,9 are fixed in a fastening element 12, so that the filter slide 1 can be brought to an end position in which the wires 6,9 act upon the contact point 5,7 in a conductive way. The fastening element 12 is fastened to the housing 13,14 of the device in which the filter slide 1 is movably held. Said contact point 5,7 is preferably arranged for transmitting modulated data.

It is always preferable that the electronic memory 4 comprises a first channel for retrieving filter-specific data, which memory is arranged as a ROM. This read-only memory cannot be manipulated and carries identification features such as serial number, batch number, production data and the like. Preferably, said ROM also comprises filter-specific data such as the influenced or chosen specific wavelength range for example.

Moreover, the electronic memory 4 preferably comprises a second channel which only allows automatic recording and retrieval of filter-specific data. Such data comprise for example the intensity and the number of the used light flashes or the used radiation dose. These data are preferably summed up in the computer and displayed to the user as a notification on the state. If a threshold value which is predetermined by the maker of the filter or the user is exceeded, then a respective alarm notification can be issued or displayed.

Moreover, the electronic memory 4 preferably comprises a third channel which allows manual recording and retrieval of filter-specific data. Such data comprise the test conditions chosen by the user for example and the respective chosen instruments.

Preferably, the electronic memory 4 comprises a back-up accumulator to avoid the loss of data due to power failure as a result of deactivating the device in which the filter slide 1 is inserted. Moreover, said back-up battery helps protect saving the data stored in the electronic memory when the filter slide 1 is removed from the device and transported or stored. It is thus ensured that the entire data stored in the electronic memory 4 are available again once the filter slide 1 is inserted into a device or is put into operation.

Even if all figures show a filter slide 1 which is arranged as a linearly movable filter carriage, the filter slide 1 can comprise an electronic memory 4 for recording or retrieving filter-specific data and a contact point 5,7 for transmitting or retrieving such data and can be arranged simultaneously as a filter wheel. Especially the second embodiment with the RFID tags is highly suitable for such a filter wheel.

A part of the invention is also a method for capturing filter-specific data in a filter slide 1 with at least one optical filter 2 for influencing light rays 3 which are used for irradiating samples or for the transmission of light through the samples or for influencing light which is reflected from the samples. Said method in accordance with the invention is characterized in that the filter slide 1 comprises an electronic memory 4 for recording or retrieving filter-specific data and a contact point 5,7 for transmitting and/or retrieving such data. In performing this method, any filter-specific data existing on the electronic memory 4 are read out in the insertion of said filter slide 1 into a device for irradiating samples or transmitting light through samples or on the activation of said device with an inserted filter slide 1.

The reading out of the filter-specific data preferably occurs via a contact point 5 which is arranged as an electric single-wire or double-wire contact and connects the device with the electronic memory 4 which is arranged as an EEPROM. The filter carriage 1 is preferably brought to a contact position for reading out the filter-specific data via the contact point 5, which contact position deviates from the respective operating position of filter 2 on the filter carriage 1. The filter carriage 1 in accordance with a first or third embodiment is acted upon with at least one spring contact for reading out the filter-specific data via the contact point 1.

Alternatively, the filter-specific data are read out via a contact point 7 which is arranged as a radio frequency or light information transmitter/receiver and connects the device with the electronic memory 4 arranged as an RFID tag. It is also preferable that the reading out of the filter-specific data occurs in a contactless manner and independent of the current position of the filter carriage 1 via a radio frequency link or a light beam connection.

The filter-specific data comprise the identification of the at least one filter and are preferably retrieved via a first channel from a ROM. The filter-specific data also comprise the recorded utilization data of the at least one filter and are preferably retrieved via a second channel which only allows automatic recording and retrieving of filter-specific data. Moreover, a third channel is preferably used, through which filter-specific data in the form of recorded additional information in connection with the at least one filter can be retrieved via a third channel. Said third channel consequently allows a manual recording and retrieval of filter-specific data.

Optoelectronic memories such as CDs (Compact Disks), DVDs (Digital Versatile Disks), holograms or three-dimensional barcodes can be used as electronic memories at least for the ROM. Principally, the ROM that cannot be overwritten by the user should be inextricably linked with the filter slide at least for this user.

"Contact point" within the terms of the present invention shall be understood as any kind of connection between the electronic memory 4 and the computer of the microplate reader.

Figure 4:
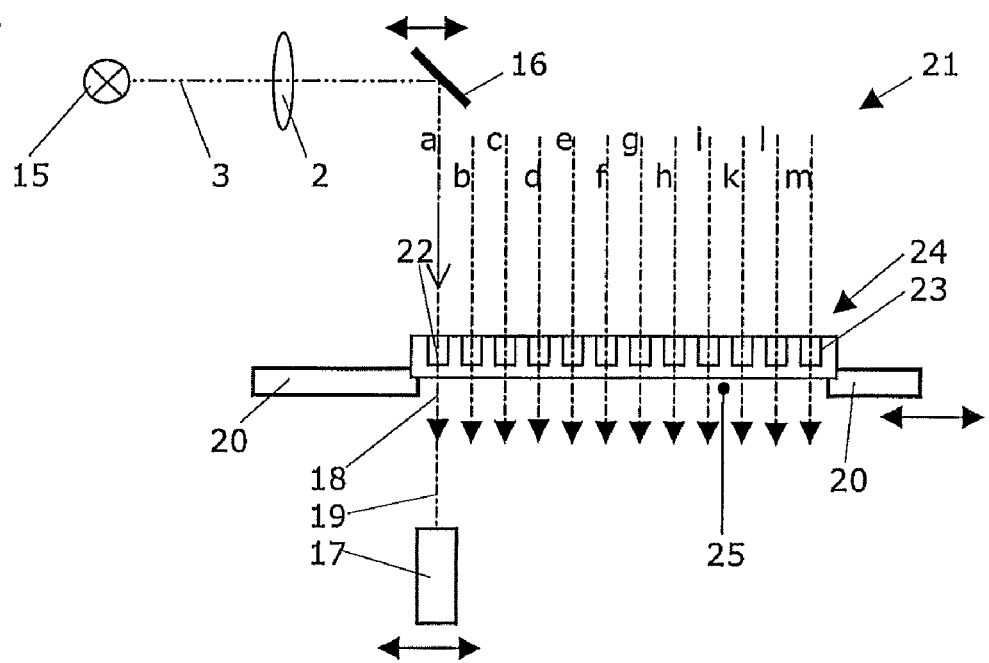
FIG. 4 shows a schematic vertical sectional view through a microplate reader.

FIG. 4 shows a schematic vertical sectional view through a microplate reader 21 for determining parameters for fluid-containing samples 22. For this purpose, the samples 22 are irradiated with light of a light source 15. This light penetrates an optical filter 2 and is then deflected with a mirror 16 in the direction towards the samples 22. The light impinges upon the samples 22 in the wells 23 in a substantially vertical direction of irradiation. The microplate reader 21 comprises a detector 17 for measuring light penetrating a sample and/or light released from a sample, and/or light reflected or scattered by a sample. In connection with the present invention, the light released by a sample and/or reflected from or scattered by a sample is called "light 18 coming from a sample". Said detector 17 is preferably situated on an optical axis 19 which is defined by the mirror 16.

It can be provided as an alternative to the illustrated embodiment that one end of an optical fiber is situated at the position of the detector 17 shown in FIG. 4, and that said optical fiber guides the light 18 coming from the probe to the actual detector. The relevant aspect is in any case that the effective direction of detection lies parallel to the optical axis 19. This can be achieved by using a fiber optic whose optical input is arranged in the desired direction of detection and whose optical output opens into the detector.

Such a detector can be arranged virtually in any desired direction and somewhere in the microplate reader 21. It measures the arriving light and provides measurement signals which are forwarded to a digital computing unit (not shown) for evaluation and display or recording. If desired, the detector can be displaced to such an extent that its optical axis coincides with the optical axis 19 of the light source 15. In this detector position it is possible to measure the 0° fluorometry or the 0° absorption of the samples. As an alternative to the mobility of the detector 17, the light source 15 or both can be mobile (cf. double arrows in FIG. 4). For the 180° fluorometry, a second detector arranged above the table 20 or a detection optic arranged above (both not shown) would be used.

For aligning the wells 23 of the microplate 24 to the optical axis 19, said microplate lies on a mobile table 20 with at least one opening 25 which is transparent for the light 18 coming from the sample. A table 20 is preferable which is mobile in the X- and/or Y-direction like an X-Y table. The wells a-m are irradiated with light from the light source 15 successively in a row for example. As an alternative to displacing the detector 17 and/or the light source 15, they can remain on site and the table 20 is displaced. In any case, the mutual displacement of table 16 and detector 17 occurs in such a way that the wells 23 with the irradiated samples 22 are positioned successively relative to the detector 17 in such a way that the light 18 released from the sample and/or reflected from or scattered by the sample (i.e. the light coming from the sample) reaches the detector 17 and can be measured by the same.

REFERENCE NUMERALS

1 Filter slide
2 Optical filter
3 Light rays
4 Electronic memory
5 Contact point
6 Contact wire
7 Contact point
8 Transmitter
9 Contact wire
10 Feed line
11 Feed line
12 Fastening element
13 Housing
14 Housing 15 Light source
16 Mirror
17 Detector
18 Light coming from the sample
19 Optical axis
20 Table
21 Microplate reader
22 Samples
23 Wells
24 Microplate
25 Opening

The invention claimed is:

1. Microplate reader with a computer for controlling the components of said microplate reader, comprising a light source for emitting light for irradiating samples or transmitting light through samples, and a filter slide situated in the excitation or detection beam path, characterized in that said filter slide comprises an electronic memory for recording and/or retrieving filter-specific data, with said filter-specific data comprising the number and intensity of the light flashes impinging upon a certain filter of said filter slide and/or the intensity and duration of all exposures performed, and that said filter slide comprises a contact point together with the microplate reader for transmitting such filter-specific data from the computer to the electronic memory of the filter slide or for retrieving such filter-specific data with the computer.

2. Microplate reader according to claim 1, characterized in that the electronic memory of the filter slide is an EEPROM, with the contact point being arranged as a single-wire or two-wire contact.

3. Microplate reader according to claim 1, characterized in that the electronic memory of the filter slide is an RFID tag, with the contact point being arranged as a radio frequency or light information transmitter/receiver.

4. Microplate reader according to claim 1, characterized in that the elctronic memory of the filter slide is a RuBee transceiver.

5. Microplate reader according to claim 1, characterized in that the contact point is arranged for transmitting modulated data.

6. Microplate reader according to claim 1, characterized in that the filter slide comprises a back-up battery for the electronic memory.

7. Microplate reader according to claim 1, characterized in that the filter slide is arranged as a filter carriage or filter wheel.

8. Method for detecting filter-specific data in a filter slide of a microplate reader according to claim 1, characterized in that filter-specific data which comprise the number and intensity of the light flashes impinging upon a specific filter of said filter slide and/or the intensity and duration of all exposures performed are transmitted by the computer via a contact point common to said filter slide and the microplate reader to an electronic memory of said filter slide and/or are retrieved with the computer from said electronic memory.

9. Method according to claim 8, characterized in that for reading in or reading out the filter-specific data the filter slide is brought to a contact position which deviates from the respective position of use of the filter on the filter slide.

10. Method according to claim 9, characterized in that the filter slide is arranged as a filter carriage and is subjected to at least one spring contact for reading in or reading out the filter-specific data via the contact point.

11. Method according to claim 8, characterized in that the reading in or reading out of the filter-specific data occurs in a contactless manner and independent from the current position of the filter slide arranged as a filter carriage via a radio frequency, magnetic or light ray link.

12. A method according to claim 8, characterized in that the filter-specific data comprise the identification of the at least one filter and are retrieved via a first channel from a memory that cannot be overwritten by the user.

13. Method according to claim 8, characterized in that the filter-specific data which comprise the number and intensity of the light flashes impinging upon a certain filter of said filter slide and/or the intensity and duration of all performed exposures are retrieved via a second channel which only allows automatic recording and retrieval of filter-specific data.

14. Method according to claim 8, characterized in that the filter-specific data comprise recorded additional information on at least one filter and are retrieved via a third channel which allows recording and retrieving filter-specific data by the user.

* * * * *